US007998195B2

(12) United States Patent
Rosenthal

(10) Patent No.: US 7,998,195 B2
(45) Date of Patent: Aug. 16, 2011

(54) DEVICE WITH ENGINEERED SURFACE ARCHITECTURE COATING FOR CONTROLLED DRUG RELEASE

(75) Inventor: Arthur L Rosenthal, Wellesley, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1285 days.

(21) Appl. No.: 11/389,712

(22) Filed: Mar. 27, 2006

(65) Prior Publication Data

US 2006/0217801 A1 Sep. 28, 2006

Related U.S. Application Data

(60) Provisional application No. 60/665,139, filed on Mar. 25, 2005, provisional application No. 60/720,808, filed on Sep. 27, 2005.

(51) Int. Cl.
*A61F 2/82* (2006.01)
(52) U.S. Cl. ...................... 623/1.42; 427/2.21; 427/2.24
(58) Field of Classification Search ................. 623/1.34, 623/1.39, 1.42–1.48
See application file for complete search history.

(56) References Cited

U.S. PATENT DOCUMENTS

| 6,395,326 | B1 | 5/2002 | Castro et al. | |
|---|---|---|---|---|
| 6,558,733 | B1 | 5/2003 | Hossainy et al. | |
| 2003/0054090 | A1 | 3/2003 | Hansen | |
| 2003/0068355 | A1* | 4/2003 | Shanley et al. | 623/1.42 |
| 2003/0144727 | A1 | 7/2003 | Rosenthal et al. | |
| 2003/0181973 | A1 | 9/2003 | Sahota | |
| 2003/0207019 | A1 | 11/2003 | Shekalim | |
| 2004/0249445 | A1 | 12/2004 | Rosenthal et al. | |
| 2005/0033417 | A1 | 2/2005 | Borges et al. | |
| 2005/0070996 | A1* | 3/2005 | Dinh et al. | 623/1.42 |
| 2005/0113903 | A1 | 5/2005 | Rosenthal et al. | |
| 2005/0228477 | A1* | 10/2005 | Grainger et al. | 623/1.42 |
| 2006/0155370 | A1 | 7/2006 | Brister | |

FOREIGN PATENT DOCUMENTS

WO WO 01/87374 A 11/2001
WO WO 2004/037443 A1 5/2004
* cited by examiner

*Primary Examiner* — David Isabella
*Assistant Examiner* — Suba Ganesan
(74) *Attorney, Agent, or Firm* — Vidas, Arrett & Steinkraus

(57) ABSTRACT

In one embodiment of the present invention a coating topology, or engineered surface architecture that may be referred to as a microdroplet deposited engineered surface architecture is provided. A plurality of drops are placed on the stent with the purpose, of building up individual units of coating material on the outer stent surface. This architecture results in a coating that uses less material, i.e., polymer, solvent, medicine, while at the same time providing for better, and determinable, drug kinetics, approaching 100% delivery and better mechanical operation of the coating binding to the stent.

16 Claims, 13 Drawing Sheets

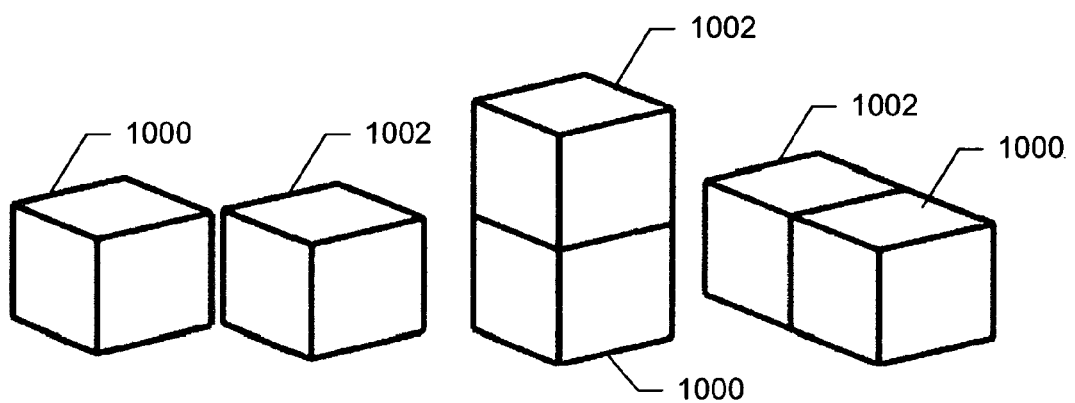
*FIG. 10A*  *FIG. 10B*  *FIG. 10C*

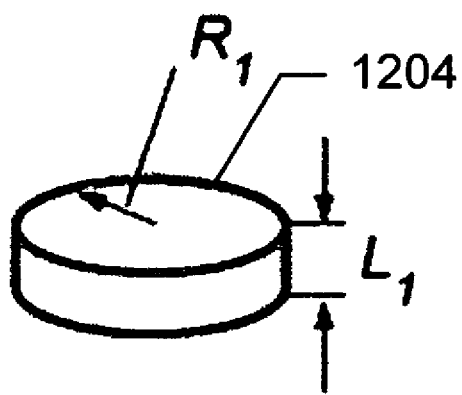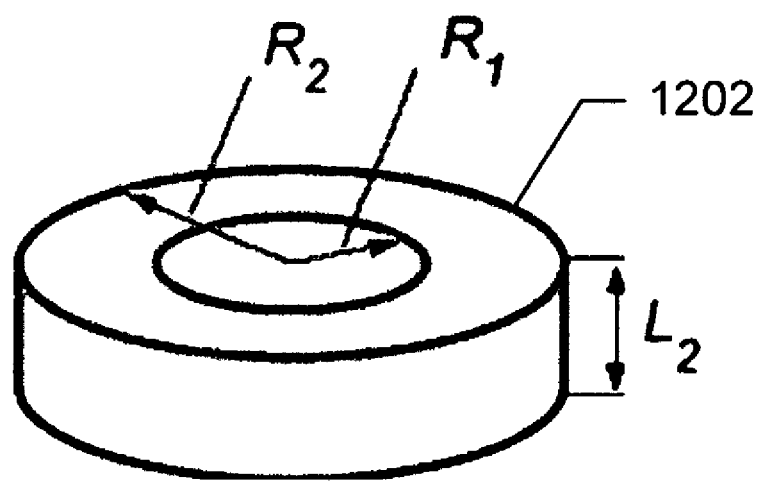
FIG. 12

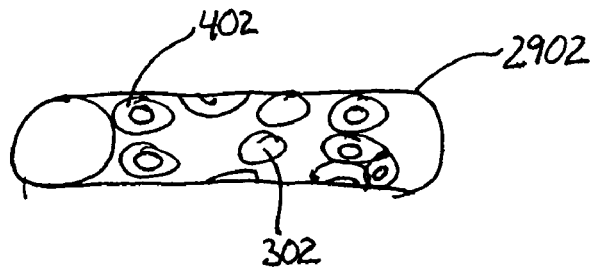
FIG. 13A
FIG. 13B
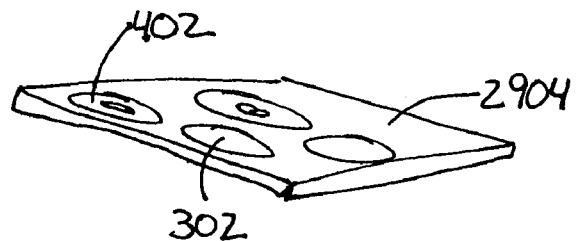
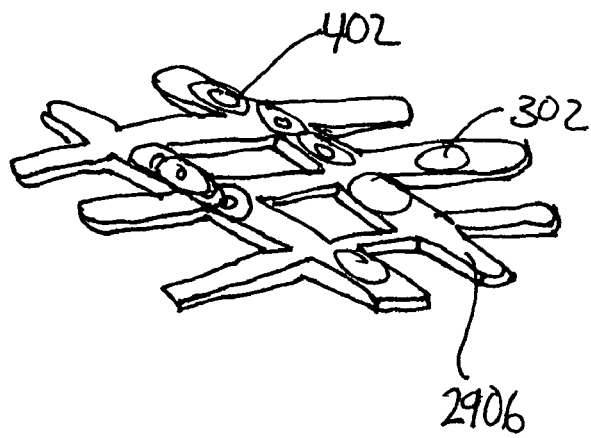
FIG. 13C
FIG. 13D
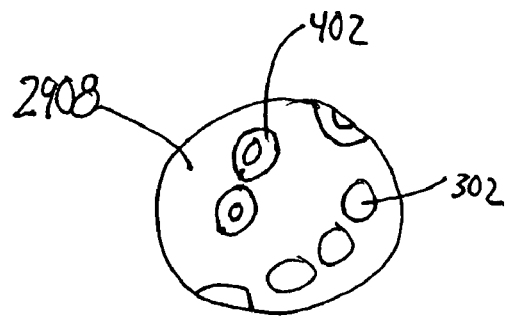

DEVICE WITH ENGINEERED SURFACE ARCHITECTURE COATING FOR CONTROLLED DRUG RELEASE

RELATED APPLICATIONS

The present application claims priority from Provisional U.S. Patent Application Ser. No. 60/665,139, filed on Mar. 25, 2005 and titled "Device With Engineered Surface Architecture Coating For Controlled Drug Release," and Provisional U.S. Patent Application Ser. No. 60/720,808, filed on Sep. 27, 2005 and titled "Device With Engineered Surface Architecture Coating For Controlled Drug Release," the entire subject matter and contents of each of which are incorporated by reference herein.

FIELD OF THE INVENTION

The present invention is directed to a medical device, e.g., a stent, with an engineered surface architecture. The engineered surface architecture includes a polymer and a drug and remains fixed to the stent surface as applied so as to provide desired drug release kinetics, drug loading and uses minimal amounts of polymer.

BACKGROUND OF THE INVENTION

Implantable medical devices are often used for delivery of a beneficial agent, such as a drug, to an organ or tissue in the body. It is intended that the drug be delivered at a controlled delivery rate over an extended period of time. These devices may deliver agents to a wide variety of bodily systems to provide a wide variety of treatments.

One of the many implantable medical devices that has been used for local delivery of beneficial agents is a vascular stent 100, an example of which is shown in FIG. 1. When coated with a material including a drug, the device is sometimes referred to as a drug-eluting stent (DES.) Vascular stents are typically introduced percutaneously, and transported intraluminally, until positioned at a desired location in the patient. These devices are then expanded either mechanically, such as by the expansion of a mandrel or balloon positioned inside the device, or expand themselves by releasing stored energy upon actuation within the body. Once expanded within the lumen, these devices become encapsulated within the body tissue and remain as a permanent implant.

Known stent designs include monofilament wire coil stents, welded metal cages, and thin-walled metal cylinders with axial slots formed around the circumference. Known construction materials for use in stents include polymers (biodegrade able and biostable,) organic fabrics and biocompatible metals, such as stainless steel, gold, silver, tantalum, titanium, cobalt based alloys, and shape memory alloys, such as Nitinol.

Of the many conditions that may be treated by stent-based local delivery of beneficial agents, one of the most important is restenosis. Restenosis is a major complication that can arise following vascular interventions such as angioplasty and the implantation of stents. Simply defined, restenosis is a wound healing process that reduces the vessel lumen diameter by either extracellular matrix deposition, neointimal hyperplasia, or vascular smooth muscle cell proliferation, and which may ultimately result in renarrowing or even reocclusion of the lumen after intervention. Despite the introduction of improved surgical techniques, devices, and pharmaceutical agents, the overall restenosis rate is still reported in the range of 25% to 50% within six to twelve months after an angioplasty procedure. To treat this condition, additional revascularization procedures are frequently required, thereby increasing trauma and risk to the patient.

Various beneficial agents placed or deposited in or on stents are known. U.S. Pat. No. 5,716,981, for example, discloses a stent that is surface-coated with a composition comprising a polymer carrier and paclitaxel (a well-known compound that is commonly used in the treatment of cancerous tumors.)

Prevention of restenosis has led to formulations intended to lengthen the amount of time over which the medicinal agent is released. The balance between an amount of polymer, solvent, and agent, in a formulation, must be established but is not currently easy to obtain. The consequences of too much agent being released too quickly can be as harmful, in come cases, as not enough agent being released. In addition, the method and structure of the deposition of the formulation on a device must be considered.

An approach to creating a drug eluting stent, or similar device, that results in a safe and effective delivery of therapeutic agent or agents is needed.

Definitions

As used herein, the following terms have the following meanings:

Abluminal: With respect to a device placed within a vessel, e.g., a stent, the surface of the stent in contact with the vessel wall, i.e., the outer surface.

Angiogenesis: The process by which a capillary network gives rise to additional branches, extensions, and connections.

Angiogenic agents: Agents that act to modulate angiogenesis.

Angiogenic factors: Angiogenic polypeptides.

Anti-inflammatory agent: Agents that act to reduce in intensity or duration the physiologic process of inflammation.

Antiplatelet agents: Agents that act to inhibit or decrease platelet aggregation and/or clot formation or otherwise modulate the aggregation and/or clotting activity of platelets. Used herein as synonymous with antithrombotic agents.

Antiproliferative agents: Agents that act to modulate cell proliferation, including cell proliferation resulting from cell transformation, for example, in the cases of cancer, malignancy, neoplasms, and virus-induced cell transformations.

Antirestenotic agents: Agents that act to modulate restenosis.

Antithrombotic agents: Agents that act to modulate thrombin activity. Used herein as synonymous with antiplatelet agents.

Arteriosclerosis: Hardening of the arteries produced by degenerative or hyperplasic changes to the intimal of arteries or a progressive increase in muscle and elastic tissue in arterial walls.

Atherosclerosis: The most common form of arteriosclerosis characterized by deposits of lipid material in the intima of medium and large diameter arteries, resulting in partial or total occlusion of an affected vessel.

Beneficial agent: As used herein, the term "beneficial agent" is intended to have its broadest possible interpretation and is used to include any therapeutic agent or drug, as well as inactive agents such as barrier layers, carrier layers, therapeutic layers, or protective layers.

Beneficial layers: Biodegradable layers comprising beneficial agents.

Biodegradable: See Bioresorbable, below.

Bioresorbable: The characteristic of being bioresorbable and/or able to be broken down by either chemical or physical processes, upon interaction with a physiological environment. For example, a biodegradable or bioerodible matrix is broken into components that are metabolizable or excretable, over a period of time from minutes to years, preferably less than one year, while maintaining any requisite structural integrity in that same time period.

Erosion: The process by which components of a medium or matrix are bioresorbed and/or degraded and/or broken down by chemical or physical processes. For example in reference to biodegradable polymer matrices, erosion can occur by cleavage or hydrolysis of the polymer chains, thereby increasing the solubility of the matrix and suspended beneficial agents.

Erosion rate: A measure of the amount of time it takes for the erosion process to occur, usually reported in unit-area per unit-time.

Hypoxia: Condition characterized by an abnormally low oxygen concentration in affected tissues.

Implantation site: A site into which a medical device or stent is physically implanted.

Ischemia: Local anemia resulting from obstructed blood flow to an affected tissue.

Matrix or bioresorbable matrix: The terms "matrix" or "bioresorbable matrix" are used interchangeably to refer to a medium or material that, upon implantation in a subject, does not elicit a detrimental response sufficient to result in the rejection of the matrix. The matrix typically does not provide any therapeutic responses itself, though the matrix may contain or surround a beneficial agent, as defined herein. A matrix is also a medium that may simply provide support, structural integrity or structural barriers. The matrix may be polymeric, non-polymeric, hydrophobic, hydrophilic, lipophilic, amphiphilic, and the like.

Openings: The term "openings" includes both through openings and recesses.

Pharmaceutically acceptable: The characteristic of being non-toxic to a host or patient and suitable for maintaining the stability of a beneficial agent and allowing the delivery of the beneficial agent to target cells or tissue.

Primarily: With respect to directional delivery, primarily refers to an amount greater than about 50% of the total amount of beneficial agent provided to a blood vessel.

Radially inner or radially interior surface: With respect to medical device struts, a radially inner or interior surface refers to a surface that has a substantially equivalent radius to that of the interior strut surface.

Radially intermediate surface: With respect to medical device struts, a radially intermediate surface refers to a surface that has a substantially equivalent radius intermediate between that of the interior and exterior strut surfaces.

Restenosis: The recurrence of stenosis after a surgical procedure, including, but not limited to, the infiltration of smooth muscle cells into the bore of a medical device implanted to correct a previous chronic occlusion.

Sequential delivery: Delivery of beneficial agents in a specified sequence, for example where about 75% of a first agent is delivered before about 50% of a second agent is delivered.

Stenosis: A restriction or occlusion of any vessel or orifice.

Therapeutic agent: Refers to any therapeutically active substance that is delivered to a bodily conduit of a living being to produce a desired, usually beneficial, effect.

Thrombosis: The formation of a thrombus (clot) within a blood vessel, often leading to partial or total occlusion of the blood vessel, leading to a condition of hypoxia in tissues supplied by the occluded blood vessel.

Vasodilators (or vasodilative agents): Polypeptides, polynucleotides encoding polypeptides, small molecules, or combinations thereof, that cause blood vessel dilation, i.e., an increase in the lumen of a blood vessel.

SUMMARY OF THE INVENTION

In accordance with one embodiment of the present invention, a medical device comprises: an abluminal surface; material disposed on the abluminal surface, the material comprising an engineered surface architecture, wherein the engineered surface architecture comprises material extending a first height from the abluminal surface and material extending a second height from the abluminal surface. The second height may be greater than the first height.

In one embodiment, the material comprises at least one of: a first drug and a first polymer in a ration by weight.

In one embodiment, the material extending the first height from the surface comprises a first ring of material; and the material extending the second height from the surface comprises a second ring of material positioned about the first ring.

In another embodiment, the material extending the first height from the surface comprises a first elliptical portion of material; and the material extending the second height from the surface comprises a second elliptical portion of material positioned about the first elliptical portion.

In accordance with another embodiment of the present invention, a device comprising: a first surface; and a plurality of discrete islands of material deposited on the first surface, wherein each of the islands of material comprises: an inner ring of material having an inner height L1 and a first radius R1; and an outer ring of material having an outer height L2, an inner radius substantially equal to the first radius R1 and an outer radius R2; wherein the second radius R2 is greater than the first radius R1 and the outer height L2 is greater than the inner height L1 is provided. The first surface may be an abluminal surface of a stent and may be porous. The island material may comprise a drug and be substantially free of polymer. The island material may comprise at least one of: a polymer and a therapeutic amount of a medicinal compound or drug. The medicinal compound is released from the outer ring of material at a first rate of release; and the medicinal compound is released from the inner ring of material at a second rate of release, wherein the second rate is greater than the first rate. The islands may be provided where: at least one island of the plurality of islands is disposed on another island of the plurality of islands; or at least one island of the plurality of islands overlaps another island of the plurality of islands; or no island of the plurality of islands is disposed on another island of the plurality of islands. The ratio of drug to polymer may be in a range of 0.5:1 to 2:1 by weight.

In accordance with another embodiment of the present invention, a method, comprising: providing a device having a first surface; and applying a first plurality of drops of a first material on the first surface, wherein the first material comprises, a polymer and a drug having a ratio, by weight, therebetween to result in a plurality of islands of material disposed on the first surface, wherein each of the islands of material comprises: an inner ring of material having an inner height $L_1$ and a first radius $R_1$; an outer ring of material having an outer height $L_2$, an inner radius substantially equal to the first radius $R_1$ and an outer radius $R_2$; wherein the outer radius $R_2$ is greater than the first radius $R_1$ and the outer height $L_2$ is greater than the inner height $L_1$, is provided.

One embodiment includes ejecting the drops of first material from an applicator, each drop with a drop volume in a range of 20-100 picoliters as ejected.

One embodiment includes determining a second plurality of target locations on the first surface of the device; and depositing an index drop of a second material on each target location, wherein substantially each drop of the first plurality of drops is deposited on a respective index drop.

One embodiment includes: placing the drops of the first plurality substantially concentrically on respective drops of the second plurality. One embodiment includes: providing the second material as comprising a polymer and a drug having a ratio, by weight, therebetween.

One embodiment includes: determining the target locations such that adjacent index drops are spaced apart from one another.

One embodiment includes: determining the target locations determined such that adjacent drops from the first plurality of drops overlap.

In accordance with one embodiment, a method, comprising: providing a device having a first surface; and applying a first plurality of drops of a first material on the first surface, wherein the first material comprises, a polymer and a drug having a ratio, by weight, therebetween, to result in a plurality of islands of material disposed on the first surface, and wherein each of the islands of material comprises: a first portion of material having a first height $L_1$; and a second portion of material having a second height $L_2$; and wherein the second height $L_2$ is greater than the first height $L_1$, is provided.

One embodiment includes: forming the material extending the first height from the surface as a first ring of material; and forming the material extending the second height from the surface as a second ring of material positioned about the first ring.

One embodiment includes: forming the material extending the first height from the surface as a first elliptical portion of material; and forming the material extending the second height from the surface as a second elliptical portion of material positioned about the first elliptical portion.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the various embodiments of the present invention only, and are presented for providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

The above and further advantages of the invention may be better understood by referring to the following description in conjunction with the accompanying drawings in which:

FIGS. 10A-10C represent a model of operation in accordance with one embodiment of the present invention;

FIG. 12 represents a model of operation in accordance with one embodiment of the present invention; and FIGS. 13A-13D are various embodiments of the present invention.

DETAILED DESCRIPTION

Figure 1:
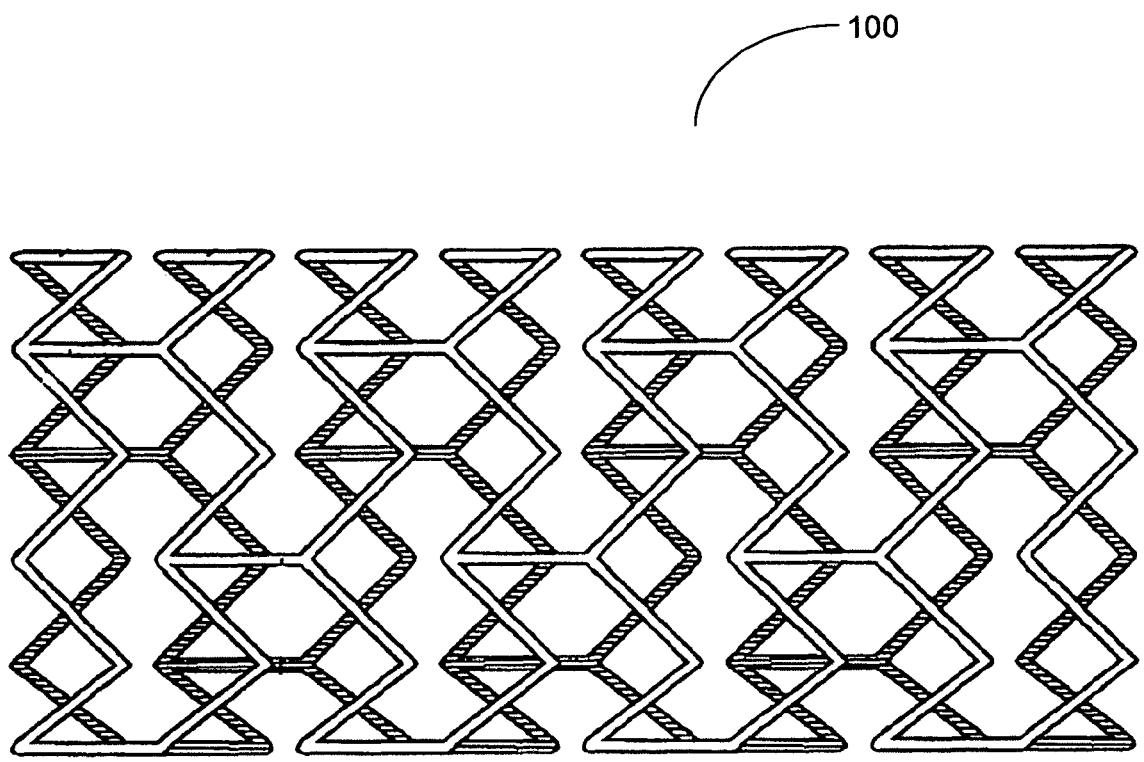
FIG. 1 is a representation of a conventional stent.

It is to be understood that the present invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

It is further appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

In the present disclosure, reference is made to a coating. It should be noted that, herein, a coating is meant to refer to application of a material, i.e., a coating material to, for example, a stent. Unless explicitly stated herein, however, coating, or the act of coating, does not imply that an entire surface is necessarily covered.

Considerations for selecting polymer and drug candidates include biocompatibility, mechanism of action of drug, stability of drug, kinetics of drug release from polymer, pharmacokinetics of tissue distribution, pharmacodynamics of the drug, persistence of the polymer, physical characteristics of coating and coatability of polymer/drug formulations.

When coating a device, e.g., a stent, a suitable drug is combined with a suitable polymer that, after application, results in a coating with defined drug loading, drug release kinetics, solids content, and coating thickness. An ideal coating would have predictable release kinetics, release the dose of drug loaded into the coating, and minimize the amount of polymer. It is desirable to establish a ratio of drug to polymer that will give desired drug release kinetics, 100% drug release and use a minimal quantity of polymer.

The properties of surface area and drug loading are important variables relating to selecting the desired drug and polymer ratio for determining a drug flow rate and a total drug flow rate, as will be discussed below. The ratio of drug to polymer, thickness, surface area and integrity of polymer are important variables that affect the rate and amount of drug release. In one embodiment of the present invention, the ratio of polymer to drug is in the range from 0.5:1 to 2:1, weight:weight with a thickness in the range of 1-10 microns.

In general, the rate and amount of drug release are measured, experimentally, by placing a coated stent into an elution solution to determine the time course and total amount of drug released from the coating. Surface area and drug loading define the concentration of drug on the surface of the coating. This relationship can be defined as: $J=kCo$ where J is the flux or drug flow rate per unit area, k is a rate constant for the transfer reaction, Co, is a constant concentration of drug at the surface or $G=AkCo$, where G is the total drug flow rate, and A is the surface area of the coating.

The amount of drug which may elute from a coating is dependent on the coating's ability to release the drug either by diffusion or disintegration of the coating over time. For coatings that are biostable, diffusion is the primary mechanism for release of the drug from the coating. As diffusion requires accessibility of the drug to a solvent (in the body this is blood or tissue fluids) low film porosity and excessive thickness may prevent quantitative drug release.

For coatings that disintegrate, e.g., bioerodible polymers, diffusion dependent release is responsible for all or part of the kinetic drug release. In the case of thick bioerodible coatings, some of the drug may be released when the polymer disintegrates.

For bioerodible polymer, it is believed that diffusion is the dominant mechanism for delivery of therapeutic material when the thickness is in the range of 1-3 microns whereas, for thicknesses greater than 3 microns, the dominant delivery mechanism is believed to be degradation. For biostable polymer, some drug is sequestered, i.e., never delivered, when the thickness is in the range of 4-10 microns.

Figure 2:
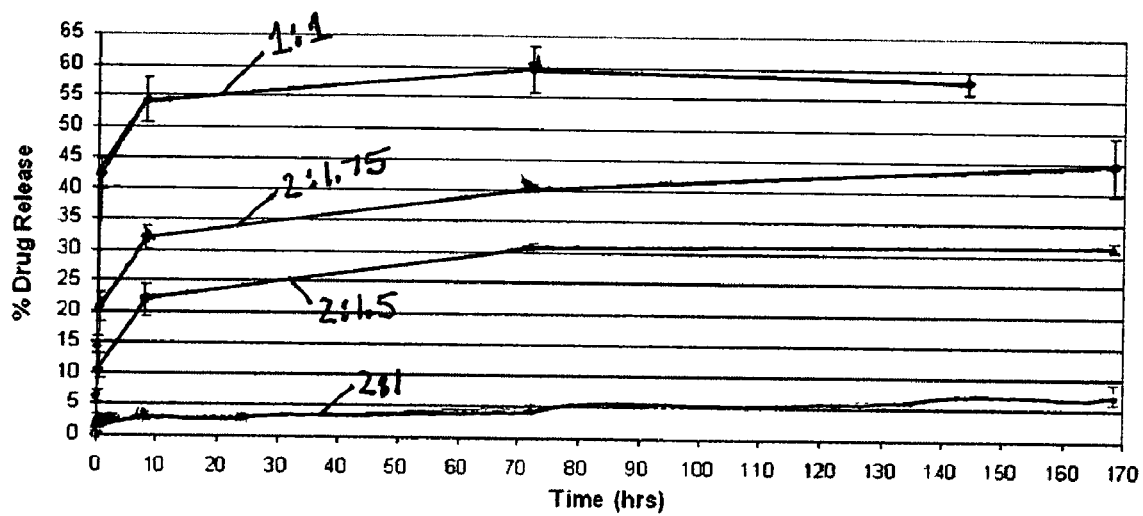
FIG. 2 is a graph showing the relative release rates for compositions of different polymer to drug ratios.

The ratio of polymer to drug in the composition affects the rate at which the drug is released. As shown in FIG. 2, as the ratio of polymer to drug (by weight) goes from 2:1 to 1:1, the amount of drug released increases. As a result, the amount of drug that is released, and the rate, can be controlled by choosing the ratio of polymer to drug.

Choosing the ratio of polymer to drug allows one to modulate the relative amounts of drug that are released due to diffusion compared to the amount of drug released due to degradation of the polymer. This, however, is only one part of the determination. The total amount of drug to be delivered and the mechanism to place that amount of drug on the device has to be determined. One embodiment of the present invention, as will be described below in further detail, addresses the drug loading issue.

Coatings should be chosen to release as much of the loaded drug as possible, ideally 100%, over a certain time period to minimize any adverse events that may occur as a result of an unexpected release of any sequestered drug. This is because the actions of some drugs, if released at some point in time significantly after the placement of the stent, could be adverse to the health of the patient.

Polymer/drug formulations applied to stents are intended to administer an active drug locally and directly to the putative site of restenosis.

The chemical and physical characteristics of polymer and drug in the coating can affect the rate of kinetic release and persistence of the polymer and drug on the stent. Such characteristics that may affect coating persistence and kinetic drug release include, but are not limited to: polymer chemistry, i.e., bioerodible or biostable, coating thickness, coating porosity, polymer basis weight, drug basis weight, and the ratio of polymer to drug.

Polymers suitable for coatings include: silicones, polyesters, polyacrylamides, SIBS, polystyrene, EVA and other such polymers with biocompatibility that can be demonstrated in, for example, porcine pig implant models.

Biocompatibility of a polymer coating is greatly affected by the amount of material in contact with tissue and blood. In the case of bioerodible polymers, the amount of material also affects persistence of the polymer. For an optimal stent coating, it is necessary to control: the amount of polymer, the thickness of coating, the consistency of coating, and to minimize the amount of coating in contact with blood.

The thickness of the coating is related to the amount of solids in the coating and the surface area over which the coating is applied. An amount of drug is chosen based on biological activity and toxicity of the drug. Polymer is added to the drug coating solution in a proportion determined to provide desired kinetic release for a desired thickness of the dried coating. The amount of drug that may be mixed with polymer is dependent on solubility conditions of the solvent coating solution and the limitations of the coating process. Even though the ratio of drug to polymer may be controlled in the coating solution, it may not be possible to dissolve the desired amount of drug and the desired amount of polymer in a solvent at the desired concentration. In order to apply the desired amount of drug to the stent surface, successive applications of coating solution may be applied to the stent surface.

The thickness of drug and polymer must be sufficient to provide coating integrity and predictable kinetic release. For a given amount of coating material, thickness of the coating will vary as a function of stent surface area coated and the amount of solids in the coating. Coating physical properties and surface concentrations of a drug are variables that affect kinetic drug delivery.

If bioerodible polymers are used in the coating, an excessive amount of drug and polymer may be present in the coating that prolongs drug delivery and increase potential for toxicity. If biostable polymers are used, the additional amount of drug may not be accessible for kinetic drug release and may be sequestered for an indefinite period of time.

Controlling the thickness of the surface coating has the beneficial effects of improving drug release kinetics including the ability to control drug release and to allow increased drug loading. Increasing coating thickness, however, results in increased overall thickness of the stent. This is undesirable for a number of reasons, including increased trauma to the vessel wall during implantation, reduced flow cross-section of the lumen after implantation, and increased vulnerability of the coating to mechanical failure or damage during expansion and implantation. Coating thickness is one of several factors that affect the release kinetics of the beneficial agent, and limitations on thickness thereby limit the range of release rates, duration of drug delivery, and the like that can be achieved. It is therefore desirable to determine a thickness to provide predictable drug release kinetics, while minimizing the amounts of drug and polymer being used.

In addition to sub-optimal release profiles, there are further problems with surface coated stents. The fixed matrix polymer carriers frequently used in the device coatings typically retain, for an indefinite period of time, approximately 30%-80% of the beneficial agent in the coating. As these beneficial agents are frequently highly cytotoxic, sub-acute and chronic problems such as chronic inflammation, late thrombosis, and late or incomplete healing of the vessel wall may occur. Additionally, the carrier polymers themselves are often highly inflammatory to the tissue of the vessel wall. On the other hand, use of biodegradable polymer carriers on stent surfaces can result in the creation of "virtual spaces" or voids between the stent and tissue of the vessel wall after the polymer carrier has degraded. These voids permit differential motion between the stent and adjacent tissue causing problems that include micro-abrasion and inflammation, stent drift, and failure to re-endothelialize the vessel wall.

There are many known processes for coating stents including, e.g., dipping, spraying, and microdroplet dispensing, i.e., the ejection of a microdroplet from a dispenser.

The dipping or spraying methods deposit the material indiscriminately on all surfaces of the stent without limitation or control. Each of these methods, i.e., spraying and dipping, has limitations with respect to at least: thickness consistency, loading accuracy, location precision and resolution.

Microdroplet deposition methods for coating provide for volumetric metering of a coating solution, thus precision and accuracy in respect of coating amount are possible. The drop volume may be controlled by ejection force, solution viscosity and tip size. Microdroplet deposition, however, requires additional mechanisms to locate the stent surface and provide coating consistency. For example, direct visual guidance, computer aided controllers, and precision metering may be necessary to apply a repeatable pattern of drops to the stent surface. Microdroplet deposition, however, cannot independently control coating thickness nor spreading on the stent surface. Viscosity, ejection force, solvent, and drop size, are variables that may independently affect spreading of a coating once applied. Coating applied to the outer (abluminal) surface of the stent may spread in all directions resulting in coating on the luminal side of the stent. Depending on the coating material applied, a coating on the luminal side of a stent might be disadvantageous.

As an example, if all surfaces of the stent are coated, then a large amount of coating/polymer would be required. If less than all surface areas of the stent are covered by the same amount of coating, then the coating would be thicker. To apply a thick coating in a small area, a large drop of solution may be applied but this drop may spread. Alternatively, a smaller drop volume of higher concentration coating solution may be used depending on solubility characteristics of the solvent. Small volumes of dilute solutions may be applied but this requires precise placement of sequential coating applications. Large drops of solution may be applied to a stent surface, however, coating may spread in all directions without predictability.

It is desirable to apply the coating over a limited surface area with a fixed ratio of drug to polymer. To do this, drop size, volume and spreading of the coating must be precisely controlled. Further, if the coating were to be specifically located on the outer surface of the stent, precise measures must be implemented to assure prior location of stent surfaces and a controlled pattern of drops.

Conventional coating approaches are directed to obtaining a continuous coating of material on the stent in order, it is believed by some, to provide a surface from which the medicinal material is best conveyed to the vessel. It is thought by some that a continuous coating will provide better mechanical characteristics, better drug delivery kinetics, higher reliability, etc. It is considered by others that the methods for coating stent surfaces, such as spraying and dipping, as well as the desired character of the coating itself: should coat the stent smoothly and evenly and provide a uniform, predictable, prolonged release of the anti-angiogenic factor. Surface coatings, in, and of themselves, however, can provide little actual control over the release kinetics of beneficial agents. These coatings are necessarily very thin, typically 5 to 8 microns. The surface area of the stent, by comparison is very large, so that the entire volume of the beneficial agent has a very short diffusion path to discharge into the surrounding tissue.

In one embodiment of the present invention a coating topology, or engineered surface architecture that may be referred to as a microdroplet deposited engineered surface architecture is provided. A plurality of drops are placed on the stent with the purpose, in one embodiment, of "building up" individual units of coating material on the outer stent surface, i.e., the abluminal surface. In other words, a microdrop structure, is provided having relatively thin and thick areas from which drug may be released at a relatively fast and slow rate, respectively. As will be explained below, advantageously this architecture results in a coating that uses less material, i.e., polymer, solvent, medicine, while at the same time providing for better, and determinable, drug kinetics, approaching 100% delivery, and better mechanical operation of the coating binding to the stent. Further, drops with different compositions, e.g., a different drug, a different polymer, and/or a different ratio of polymer to drug, may be alternatingly deposited, either laterally along the surface of the device, or vertically, i.e., one atop another or overlapped to an extent.

Specific coating parameters may be controlled to produce the desired size and/or characteristics of the engineered surface architecture. In one embodiment, a solution of drug and polymer are dissolved in a compatible solvent at a desired ratio and placed into the JAC™ System from Labcoat, Ltd., of Galway, IR as described in U.S. Pat. No. 6,645,547 to Shekalim, et al., issued Nov. 11, 2003 and titled "Stent Coating Device," and US Publication 20030207019A1 to Shekalim et al., published Nov. 6, 2003 and titled "Stent Coating Device," the entire contents of each of which are incorporated herein by reference.

A drop size, i.e., the size of the drop or microdroplet to be ejected from an applicator and toward the stent, is chosen to be in the range of 30-60 microns depending on the width of the stent surface. A pattern of between 2000-2500 targets or target points, for example, is selected along the center line of the stent surface. The viscosity of the solution is adjusted so as to produce microdroplets of coating solution in the range of 20-100 picoliters as ejected. In one embodiment, the coating process, via ejection of microdroplets, first places an index microstructure on the surface at each of the target points. Successive microdroplets are deposited on top of each of the already placed microstructures, depending on the amount of drug desired. In one embodiment, the formulation is provided such that the drops remain only on the abluminal surface and do not spread to a sidewall of a stent strut. The thickness of the engineered surface architecture may be controlled by the drops' diameter and by the amount of solids in the coating solution.

The index drop may comprise a primer or other material to facilitate placement of subsequent drops. In addition, the index drop may comprise polymer that is the same as the polymer of subsequent drops.

A drug is chosen based on desired chemical and biological characteristics including therapeutic index, solubility and compatibility with polymer carrier. The polymer and drug are dissolved in a solvent in which both agents are miscible at the desired final concentration of both polymer and drug. The polymer and drug are solubilized at a fixed ratio to prepare a coating solution. The concentrations of both polymer and drug in the coating solution are adjusted so as to result in a stent coating of known amount of drug and polymer and coating thickness after deposition and drying. The amount of drug applied in the stent coating is determined by knowing the therapeutic dosage of the drug, the toxicity level of the drug and the surface area of vessel wall of the vessel after full stent expansion.

Many polymers may provide the appropriate chemical properties for formulating stent coatings. Such polymers may have desired chemical properties yet are not sufficiently biologically compatibility because the amount and physical characteristics of the coating may affect biocompatibility. In addition, for bioerodible polymers, the amount of polymer in the coating may affect the rate of degradation of the coating. Choosing appropriate polymers and amount of polymer in the coating requires careful testing in suitable animal models, typically, rabbit and porcine implant studies. For example, a polylactic acid, a high molecular weight bioerodible organic ester, is known to have suitable chemical and physical properties for stents and stent coatings. In studies conducted with high amounts of polylactic acid and other such polyesters, tissue inflammation has been correlated with the amount of polymer associated with the tissue. Stents coated with 10 ug/75 mm$^2$-30 ug/75 mm$^2$ vessel wall polylactic acid polymer, are essentially indistinguishable from stents without coatings.

The topology of the present invention is created by placing microdroplets substantially concentrically co-located on the stent surface. In other words, microdroplets are repeatedly placed at substantially the same locations to either "stack-up," i.e., build additively, as islands of coating material or to create discoids of coating material. These will be discussed below in more detail.

Advantageously, because the ratio of polymer to drug and the volume of each drop are known, then the amount of drug in a drop is determinable. If a particular amount of drug is to be deposited on the device, then the required number of drops can be calculated and applied. The structure of the present invention provides the desired amount of medicine with the minimum amount of polymer. As is known, reducing the amount of polymer introduced into the vasculature can be beneficial.

Figure 3:
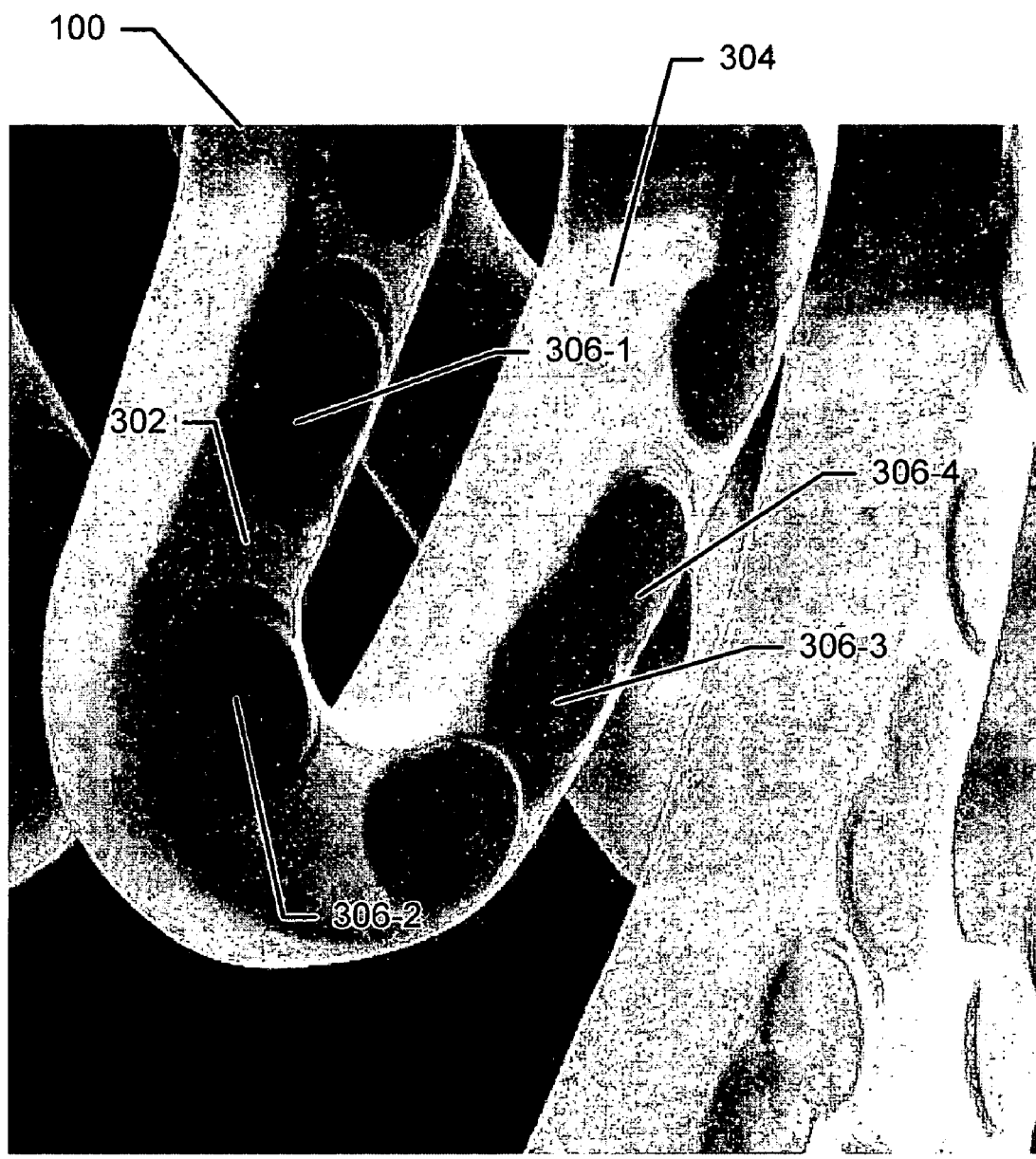
FIG. 3 is a representation of a stent with a surface architecture in accordance with one embodiment of the present invention.

These islands of coating material may be spaced apart such that adjacent islands either are separated from one another by a section of stent surface that has substantially no coating material, or a surface that is pre-coated or "primed" with a different material located thereon, or may be placed such that the islands overlap. As shown in FIG. 3, a stent 100 includes an abluminal surface 302 and a sidewall surface 304. A first island 306-1 is separated from an adjacent island 306-2 by a space on the abluminal surface 302. As is shown in FIG. 3, a number of these islands 306, generally, are placed substantially along the abluminal surface 302 of the stent 100. The choice of solvent, solvent ratio to polymer, ratio of medicine or drug to polymer, microdroplet size at ejection, drop ejection velocity, and other characteristics of the coating material contribute to aspects of the island building. In one embodiment, the islands have a center portion that is higher than its periphery. In another embodiment, the island is substantially planar.

Alternatively, the islands are positioned such that adjacent islands overlap with one another. As shown in FIG. 3, adjacent islands 306-3 and 306-4 are positioned to overlap. According to one embodiment of the present invention, overlapping and non-overlapping islands of material can be placed on the same medical device or stent. The determination to overlap or not, on a specific section of the stent, may be a function of the geometry of the stent as well as the intended placement location within the vasculature. It is further envisioned that portions of a stent will be coated differently than other portions.

Figure 4:
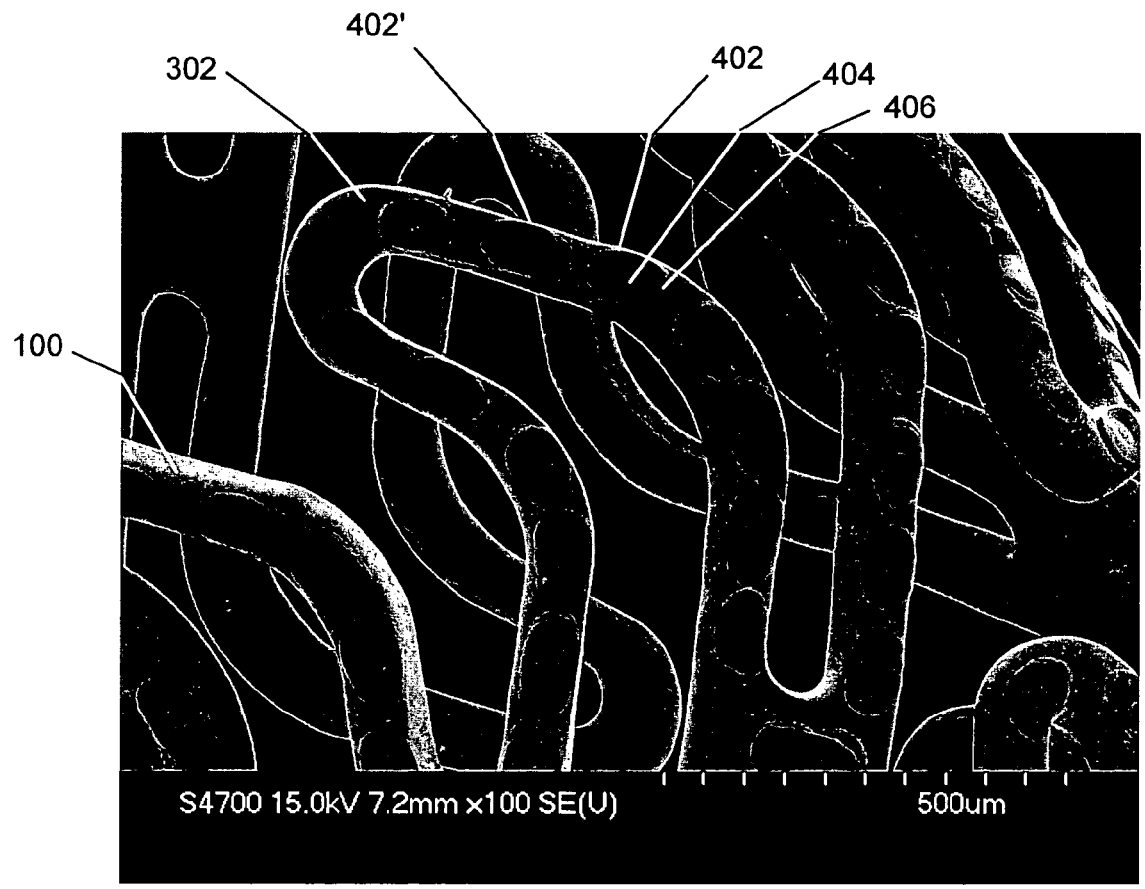
FIG. 4 is a representation of a stent with a surface architecture in accordance with another embodiment of the present invention.
Figure 5:
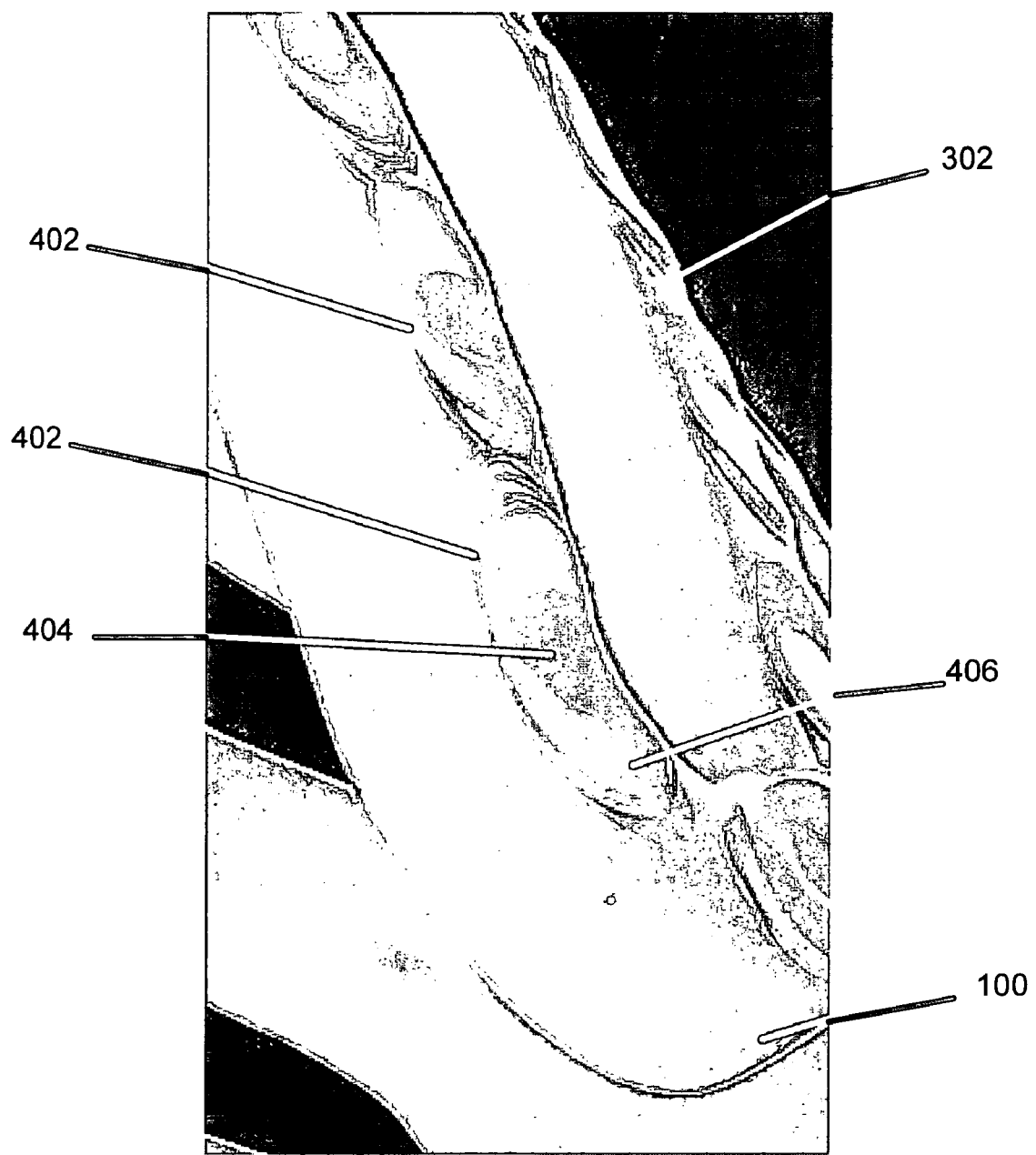
FIG. 5 is an alternate view of the stent with the surface architecture as shown in FIG. 4.

Depending upon the solvent used, the substantially concentric placement of microdrops may result in a surface architecture comprising a plurality of discoids, i.e., a disc-shaped deposit or microstructure. A discoid may be considered as a type of island. As shown in FIGS. 4 and 5, a stent 100, has, on its abluminal surface 302, a first discoid 402 that includes a central portion 404 where substantially most of the coating material has either evaporated away, due to the flash point of the solvent, or has "splashed" or "spread out" to create the side portions, or a ring 406 about the central portion 404. The choice of solvent, drop velocity and drop size contribute to the discoid's shape and size. As is also shown in FIG. 4, an adjacent discoid 402' is spaced from the first discoid 402 a sufficient distance along the abluminal surface 302 so as to avoid overlap.

Figure 6:
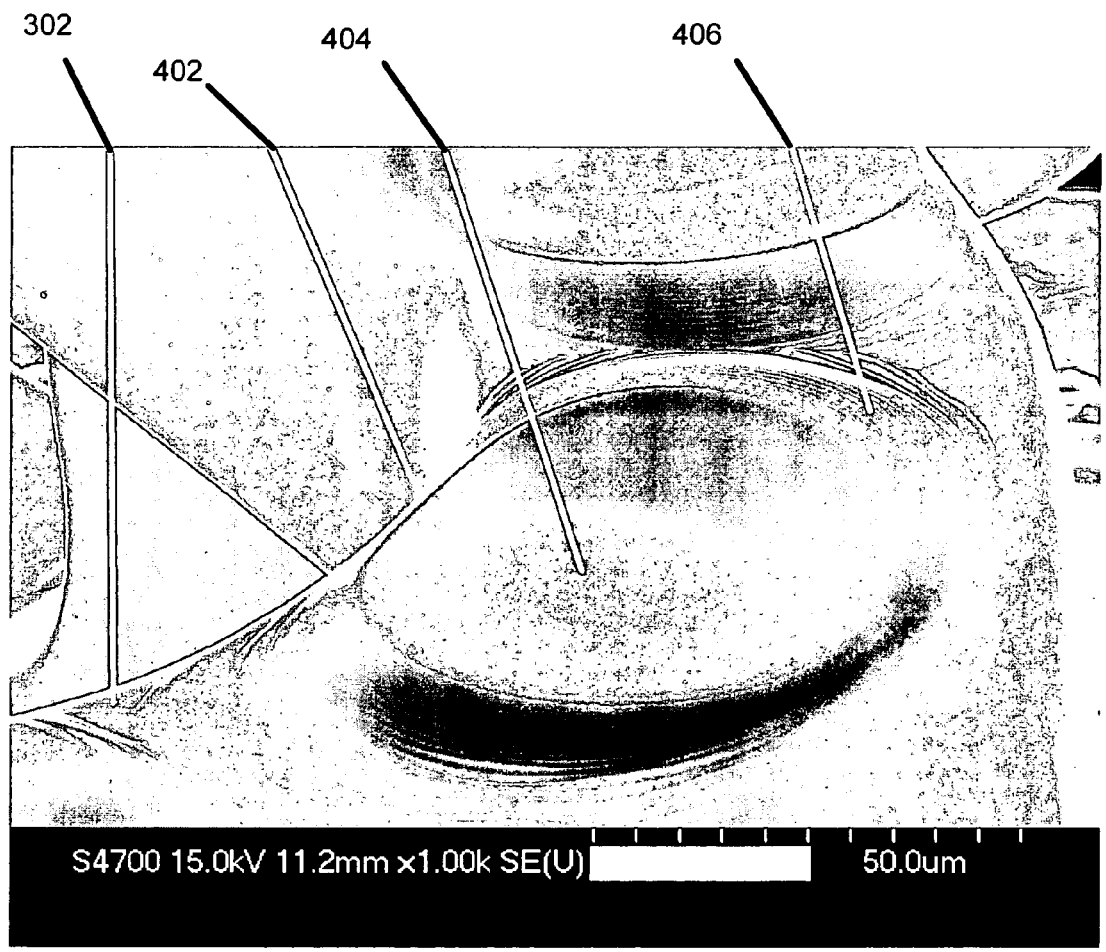
FIG. 6 is a close-up representation of one of the surface architectural features in accordance with one embodiment of the present invention.

The discoid 402 includes the central portion 404 and the side portion 406, as shown in a close-up view in FIG. 6. As mentioned above, the central portion 404 is a result of the combination of the evaporation of solvent used to dissolve the drug in the polymer and the velocity with which the successive droplets impact the abluminal surface 302 of the stent 100. Advantageously, due to the selection of the parameters of the droplet, the material is effectively placed within a determinable location. Further, the amount of drug, accumulated by the successive placement of the drops, to be found within the side portion 406 is known. Finally, as will be discussed below, the rate at which the drug will be released is determinable as a function of the polymer to drug ratio.

Figure 7:
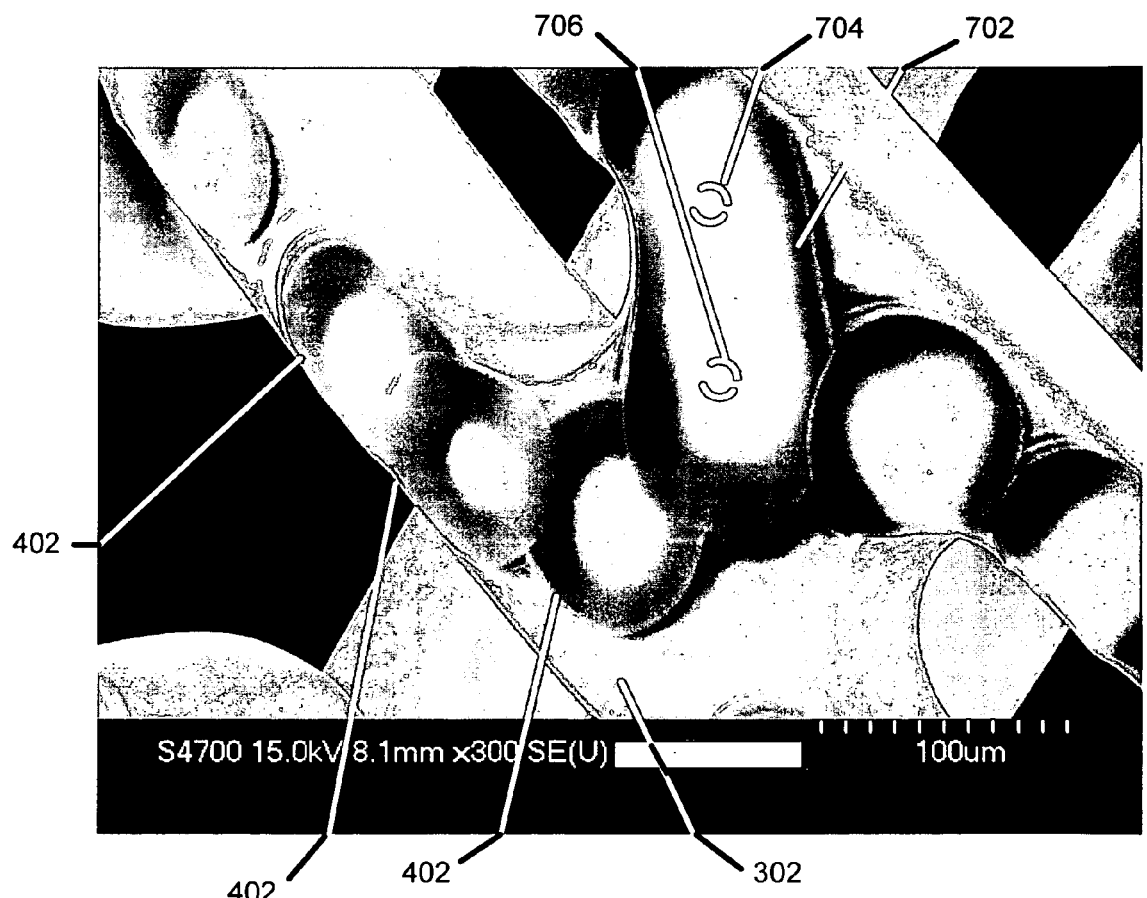
FIG. 7 is a representation of a stent with a surface architecture in accordance with another embodiment of the present invention.

Alternatively, as shown in FIG. 7, discoids 402 may be placed in proximity to one another in order to overlap. In accordance with one embodiment of the present invention, a time period between placement of adjacent drops on the surface of the stent 100 is chosen, taking into consideration evaporation rates, boiling point, etc., in order to cause the overlapping. In addition, the locations of the adjacent drops can be chosen to cause a "joining" of the two discoids into one, as represented by a discoid 702 shown in FIG. 7. The discoid 702, in one embodiment, is created by placing respective drops at locations 704 and 706. The subsequent spreading and evaporation, that is, the "blending" or "merging" together of side portions, results in the "elongated" discoid 702.

Advantageously, separated, overlapped discoids 402 and/or elongated discoids 702 may be placed at specific regions of the stent 100 to accommodate mechanical attributes of the stent 100. As an example, at portions of the stent 100 where there is high mechanical stress, the discoids 402 may be non-overlapped to provide resistance to axial stress crack propagation and better mechanical integrity of the coating on the stent. At other portions of the stent 100, the discoids may be overlapped to deliver the drug.

Figure 8:
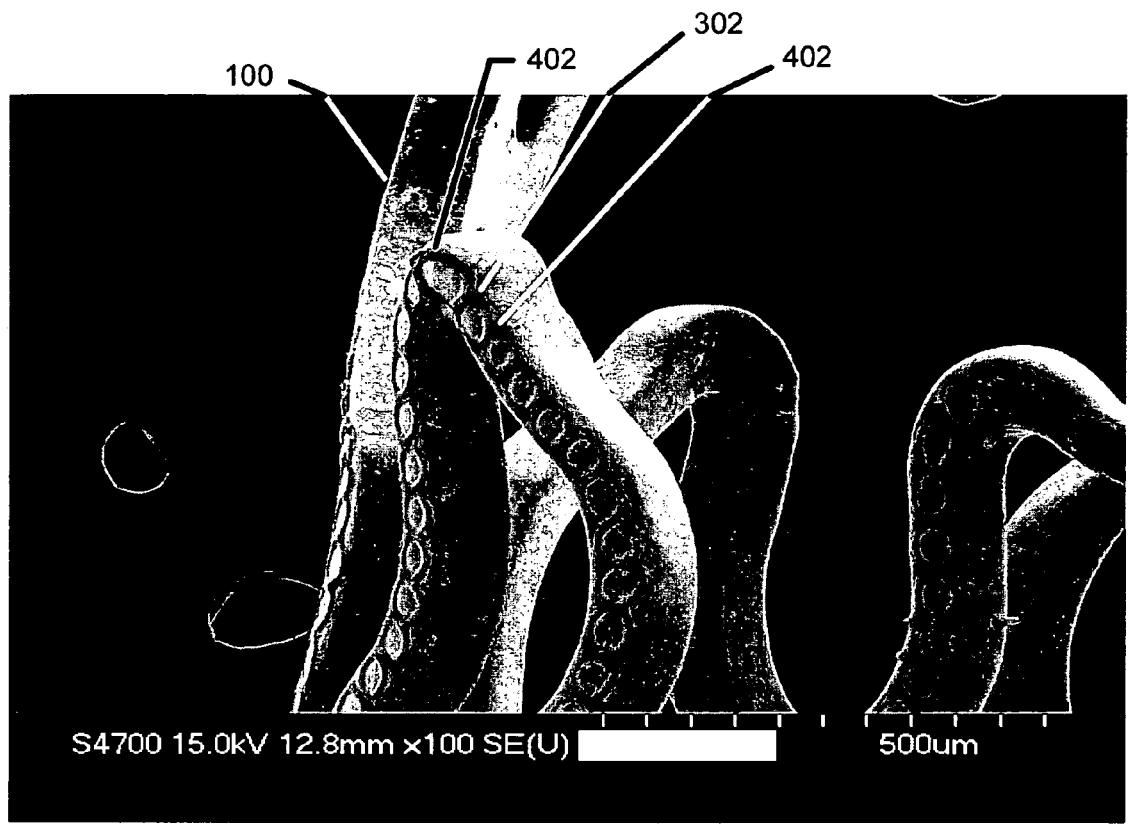
FIG. 8 is a representation of a stent with a surface architecture in accordance with another embodiment of the present invention.

In accordance with another embodiment of the present invention, discoids 402 are deposited on the abluminal surface 302 of the stent 100 with a spacing that causes the outer portions 406 of adjacent discoids 402 to abut. As shown in FIG. 8, a "chain" of discoids 402 is provided on the abluminal surface 302. The placement of multiple droplets at substantially the same locations allows for the "buildup" of the outer portions 406. As described above, because the amount of drug in each droplets is known, a desired total amount of drug can be deposited by choosing the necessary number of droplets. Further, the elution profile can be tailored as a function of the polymer to drug ratio of the droplet composition.

It should be noted that parameters which may affect the microdrop structure and drug dispersion within the microdrop include solvent evaporation, frequency of jetted drops, time of flight for drop to land, distance between microdrops on the stent surface and time between sequential deposition of drops.

The drop as jetted must be stable in order to repeatably deposit a predictable and regular quantity of material. From the time the drop is jetted until it lands, evaporation must be minimal. Therefore, time of flight must be small compared to the evaporation rate of solvent in the formulation. Once the drop lands, the solvent must evaporate to "fix" the coating to the stent surface and this spot becomes the foundation of the microdrop for the remainder of the sequential passes.

If a linear coating protocol is used to apply drops with a space on the abluminal surface therebetween, each subsequent drop must be applied after the previous drop is dry and/or at a sufficient distance from the previous drop to insure that drops remain discrete from each other. Accordingly, by controlling the time and/or distance between adjacent drops, one can control the surface microdrop structure.

Drops can be applied by controlling either the spacing or the time between sequential drops so that each previous drop has sufficiently dried prior to the application of a further sequential drop. By this method, each microdrop has a homogenous composition wherein the drug and polymer ratio are fixed through the entire volume of the drop. The release rate is then determined by surface area to volume ratio of the microdrop in general and the relative surface area and volume of the relatively thin (fast) and thick (slow) regions of the microdrop, specifically.

The results seen for the drug elution kinetics of a stent with the engineered surface architecture according to the embodiments of the present invention have been mathematically modeled to present one theory regarding the operations that are occurring. The data fit into several possible models of drug eluting coating—each of which describe the drug release process as an event with two stages.

In the first stage, the drug located near the surface of the coating is washed out at a faster rate than the drug from an interior layer of the coating domain. There is also a "bulk" region of the coating domain from which the drug is not being released on the same timescale as the other layers.

Figure 9A:
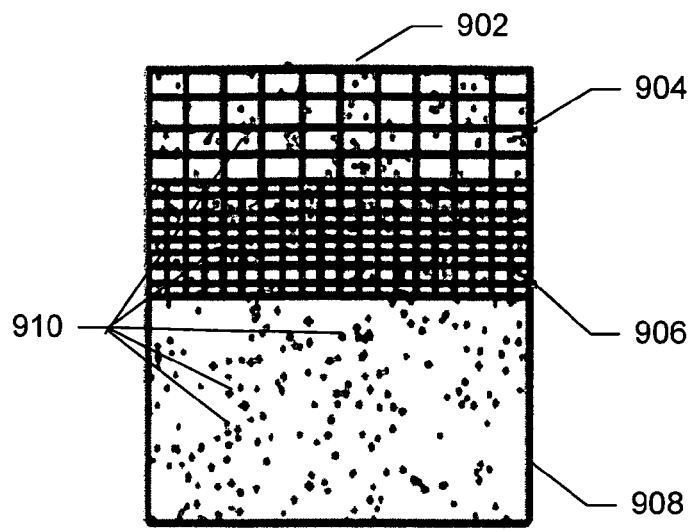
FIGS. 9A-9C represent a model of operation in accordance with one embodiment of the present invention.
Figure 9B:
Figure 9C:
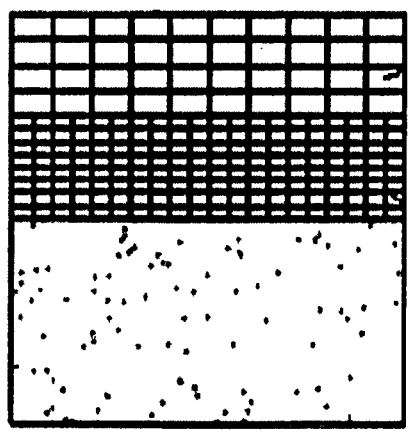

The stages of the process are schematically represented in FIGS. 9A-9C. As shown in FIGS. 9A-9C, an active surface 902 represents the top of the discoid or island of material. A boundary layer 904, a sub-boundary layer 906 and a bulk region 908 include varying amounts of drug 910. It is assumed that: a) the drug 910 is released from the boundary layer 904 so quickly that it does not noticeably affect the dynamics of drug release from the sub-boundary layer 906; b) after the drug 910 is gone from the boundary layer 904, the porosity of the boundary layer 904 increases to such an extent that the drug 910 that leaves the sub-boundary layer 906 and enters the boundary layer 904 can be considered as entering the outside bulk liquid, i.e., the tissue; c) concentration of drug 910 in the bulk region 908 does not change; d) the initial drug concentration in the coating is assumed to be constant throughout the coating domain; and e) there is no drug elution through the side boundaries of the coating domain.

In one example, the creation of islands of coating material has been modeled to characterize the dynamics of the kinetics of the medicinal component of the coating. The surface topology or engineered surface architecture (ESA) described herein has been modeled as two parallelepipeds 1000, 1002 with constant volume that are either disconnected, connected vertically, or connected horizontally as shown in FIGS. 10A, 10B, and 10C, respectively. In the analysis, if the height of an individual basic domain changes, so does the area of its horizontal cross-section but the volume of such elementary domain stays the same. In the modeling analysis, it is assumed that (1) the boundaries corresponding to top and side surfaces of coating domain are drug permeable. The bottom surface is assumed to be isolated. The drug is leaving the domain through the top and side (active) surfaces. It is also assumed that (2) the drug from the coating enters an infinite volume of liquid in which the drug is infinitely (instantly) soluble.

The mathematical modeling analysis showed that the fastest time decay of the total amount of drug is observed for two disconnected elementary domains. For shorter elementary heights of a certain ratio of height L to volume V, the drug decay is slower for vertically connected domains, while for taller elementary domains, a different ratio of height L to volume V, the drug decay is slower for horizontally connected domains. The slowest possible drug decay rate for vertically connected domains corresponds a calculable ratio of height L to volume V as does the drug decay rate for horizontally connected elementary domains.

Figure 11:
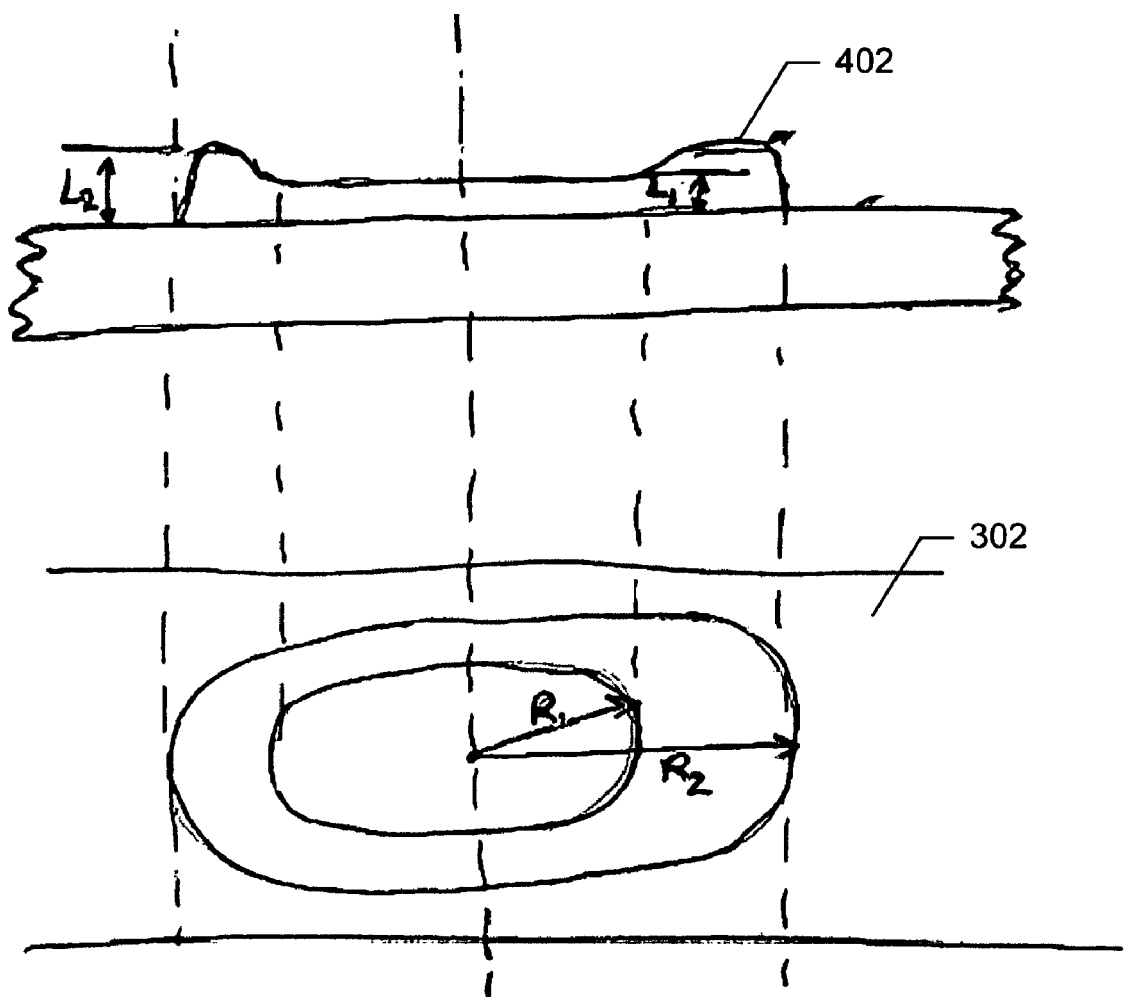
FIG. 11 represents a model of operation in accordance with one embodiment of the present invention.

The discoid 402, as shown in the figures can be schematically represented as shown in FIG. 11. As shown, the discoid 402 has an outer radius $R_2$ and an inner radius $R_1$. The discoid 402, between $R_2$ and $R_1$, has an outer height of $L_2$ and the inner radius has an inner height $L_1$. As can be seen, the discoid is positioned on the stent surface 302. It is possible that, in one embodiment, the inner height $L_1$ is substantially zero (0) when measured from the stent's surface 302.

The discoid 402 can be mathematically modeled as shown in FIG. 12 by normalizing its shape to that of a cylinder 1202 with a missing or diminished portion 1204 in the middle. The mathematical analysis showed that, where the total volume of a droplet, and thus the total drug load is constant, the amount of drug released on a fast time scale is going to be defined by the height and width of the interior part of the discoid (with smaller height) and the amount of drug released on a slow time scale is going to be defined by the height and width of the exterior part of the discoid (with greater height.)

Alternatively, the discoid may be constructed so that L2 may be constructed to have multi boundary layer conditions such that the diffusion rate from L2 is not uniform. For example, the height of L2 may be constructed so that the upper portion is a fast release domain, the sublayer is a moderate release domain and the lower is essential a no release domain within certain defined time points. It follows that a discoid may be constructed to tailor the rate and amount of drug release by varying its diameter, height and volumes of the inner and outer discoid components.

Further, a discoid may be constructed with multiple drugs and different polymers so that either the inner portion or outer portion my act as independent drug delivery mechanisms having variable amounts and rate of respective drug release.

In other examples, a discoid can be considered to release drug from all surfaces or specifically defined surfaces.

The microdroplet architecture has other advantages. In one embodiment the coating may be placed on only a portion of the stent in order to "tune" the application of the medicine.

It should be noted that a bare stent may be "primed" with an underlying coating of material or "primer" that is allowed to set prior to the coating containing the medicinal coating being applied. Thus, with respect to the foregoing embodiments, the areas of the abluminal surface between the islands 302 or discoids 402 may be covered with the primer material and not be a bare stent surface. The primer may include a first medicine, different from any medicine or medicines or drugs, in the coating of the engineered surface architecture.

In one embodiment, a stent or medical device may be coated over all of its surfaces, e.g., for a stent—there may be coating on the luminal and abluminal surfaces in addition to the sides of the struts. This coating may be found on a device that has been coated by a dipping process. It is known to provide a stent over all surfaces with a first coating solution containing heparin. Thus, a stent already coated with heparin, for example, would then have the coating with the engineered surface architecture applied thereon. Further, a stent or device may be initially provided with a bio-beneficial coating such as titanium oxide on which the engineered surface architecture can be deposited.

Further, the present topology allows for the placement of the coating to accommodate known stress points on the stent. There are locations on the stent that are known to be subject to high stress levels because of the mechanics of the stent, especially when the stent transitions from its compressed state to its expanded state. These locations on the stent represent the points where the coating is most likely to separate from the stent surface. According to one embodiment of the present invention, the number of drops in these areas can be adjusted to minimize the chance of the coating being separated from the stent when the stent is mechanically stressed. This tailoring of coating placement leads to higher reliability of the stent coating.

The topology described above allows for the elution rate to be controlled by defining the shape, size and number of locations at which the coating material is placed. In this manner, the surface area from which the drug is eluted is controlled and predetermined. The stent architecture no longer controls the amount of coating material that will be deposited.

Stents must be mounted on a delivery device to implant the stent within the vessel. Most commonly, stents are mounted on catheter balloons by mechanical crimping causing the inner surface of the stent to adhere to the balloon surface. In the case of stents having coating material on the inner surface, direct contact on balloon and coating material result. Such contact on the balloon and coating material is an undesirable result and may cause migration of drug into the balloon material, transfer of balloon materials to the coating, sticking of the balloon and stent coating, and mechanical disruption of the inner coating surface upon balloon expansion. The result of such balloon and coating material interactions may cause difficulty in placing the stent or undesirable biological consequences to the patient.

Microdroplet surface structures applied substantially to the outer surface of the stent to create the engineered surface architecture avoid the interaction between balloon material and coating and thus eliminates a potential downside of stent coatings.

While embodiments of the foregoing description were directed to placing the engineered architecture upon the stent surface by microdroplet deposition, it is envisioned that other mechanisms for creating the architecture are possible. It may be possible to use a dipping or spraying method with masking techniques in addition to vapor deposition or plasma etching of some type. Any one of a number of lithographic techniques may also be suitable for creating the engineered architecture. Further laser etching may also be used in conjunction with, for example, a photoresist polymer. The resulting engineered architecture, as described herein, is not limited to a particular mechanism of manufacture.

The engineered surface architecture (ESA) can be applied to almost any medical device, e.g., a stent, as has been described. A normally uncoated stent, i.e., one that has not been coated by its manufacturer, may have the ESA placed thereon without need for any mechanical modification to the stent. As an example, reservoirs or holes in a stent's struts are known for being filled with medicine to be released into the vessel. These holes, however, can affect the mechanical performance of the stent and add to the manufacturing complexity of the stent. The ESA described herein can be applied to a known stent without the need for mechanical modifications such as the adding of holes. Thus a physician may be able to choose a known stent and apply a customized ESA to coat the stent for a particular patient's requirements.

Further, the engineered surface architecture of the present invention may be applied to a device having a porous surface. In one embodiment, the drops placed on the surface do not comprise any polymer.

Still further, one of ordinary skill in the art will understand that different polymers have different structures, i.e., porosity, that contributes to the rate at which a drug will diffuse. The larger pores contribute to a faster diffusion rate. In accordance with one embodiment of the present invention, the pore size of a polymer can be accommodated by adjusting the ratio of polymer to drug to attain the desired drug elution kinetics.

While conditions relating to the narrowing of arteries represent the majority of situations that call for stents, coated or not, there are other medical conditions that may warrant the use of a medical device with the engineered architecture as described herein.

Vulnerable plaque is a condition that cannot usually be easily seen but which is detectable and, in some cases, treatable. With vulnerable plaque, a lesion forms in the vessel and may go undetected until the lesion bursts quickly, often leading to a sudden death.

Drugs are available to treat vulnerable plaque, however, delivery to the site of the lesion is problematic. A delivery device or drug applicator with the engineered architecture of this disclosure may be manufactured and delivered to the site of the lesion. The device does not have to be a stent, as the "scaffolding" function of a stent may be unnecessary at the location of vulnerable plaque. Rather, an erodible structure may be provided at the site of the lesion.

Further, while the engineered architecture is suitable for intraluminal devices in order to provide a topology with better drug delivery characteristics, the topology is also applicable to devices that may be delivered sub-dermally. In this application, the desired delivery dynamics can be tailored based upon the shape(s) of the engineered architecture.

One of ordinary skill in the art will understand that other implantation devices, aside from stents, can have the engineered architecture applied thereto and are envisioned as falling within the concepts of this disclosure as shown in FIGS. 13A-13D. Similar to a stent, a cylinder 2902, either hollow or solid, and made from a bio-compatible material, is envisioned to have the engineered architecture including the discoids 402 and/or the islands 302, described above. In addition, and also as described above, the discoids 402 and islands 302 are either separated from adjacent ones or deposited upon one another, depending upon the desired performance characteristics.

In another embodiment, a planar device 2904 is also provided with the engineered surface architecture including discoids 402 and islands 302 either separately, together, overlapping or adjacently positioned.

In another embodiment, a mesh structure 2906 is also provided with the engineered surface architecture including discoids 402 and islands 302 either separately, together, overlapping or adjacently positioned.

In yet another embodiment, a sphere 2908 is also provided with the engineered surface architecture including discoids 402 and islands 302 either separately, together, overlapping or adjacently positioned.

The cylinder, planar device, mesh structure and sphere can be made of any material that can be placed within the body, either intraluminally or subdermally. This material, as known to one of ordinary skill in the art, include, but are not limited to, stainless steel and nitinol. Further, any one or more of these embodiments may be made from a biodegradable material that dissolves at some point in time after implantation.

The engineered architecture is useful for, for example, delivering antirestenotic, antithrombotic, antiplatelet, antiproliferative, antineoplastic, immunosuppressive, angiogenic, antiangiogenic agents, anti-inflammatories, and/or vasodilators, in addition to other compounds listed below, to a blood vessel. The present invention is particularly well suited for the delivery of antineoplastic, angiogenic factors, immuno-suppressants, and antiproliferatives (anti-restenosis agents) such as paclitaxel and Rapamycin for example, and antithrombins such as heparin, for example.

Therapeutic agents for use with the described embodiments may, for example, take the form of small molecules, peptides, lipoproteins, polypeptides, polynucleotides encoding polypeptides, lipids, protein-drugs, protein conjugate drugs, enzymes, oligonucleotides and their derivatives, ribozymes, other genetic material, cells, antisense oligonucleotides, monoclonal antibodies, platelets, prions, viruses, bacteria, eukaryotic cells such as endothelial cells, stem cells, ACE inhibitors, monocyte/macrophages and vascular smooth muscle cells. Such agents can be used alone or in various combinations with one another. For instance, anti-inflammatories may be used in combination with antiproliferatives to mitigate the reaction of tissue to the antiproliferative. The therapeutic agent may also be a pro-drug, which metabolizes into the desired drug when administered to a host. In addition, therapeutic agents may be pre-formulated as microcapsules, microspheres, microbubbles, liposomes, niosomes, emulsions, dispersions or the like before they are incorporated into the matrix. Therapeutic agents may also be radioactive isotopes or agents activated by some other form of energy such as light or ultrasonic energy, or by other circulating molecules that can be systemically administered.

Exemplary classes of therapeutic agents include antiproliferatives, antithrombins (i.e., thrombolytics), immunosuppressants, antilipid agents, anti-inflammatory agents, antineoplastics including antimetabolites, antiplatelets, angiogenic agents, anti-angiogenic agents, vitamins, antimitotics, metalloproteinase inhibitors, NO donors, nitric oxide release stimulators, anti-sclerosing agents, vasoactive agents, endothelial growth factors, beta blockers, hormones, statins, insulin growth factors, antioxidants, membrane stabilizing agents, calcium antagonists (i.e., calcium channel antagonists), retinoids, anti-macrophage substances, antilymphocytes, cyclooxygenase inhibitors, immunomodulatory agents, angiotensin converting enzyme (ACE) inhibitors, anti-leukocytes, high-density lipoproteins (HDL) and derivatives, cell sensitizers to insulin, prostaglandins and derivatives, anti-TNF compounds, hypertension drugs, protein kinases, antisense oligonucleotides, cardio protectants, petidose inhibitors (increase blycolitic metabolism), endothelin receptor agonists, interleukin-6 antagonists, anti-restenotics, and other miscellaneous compounds.

Antiproliferatives include, without limitation, sirolimus, paclitaxel, actinomycin D, rapamycin, and cyclosporin.

Antithrombins include, without limitation, heparin, plasminogen, .alpha.sub.2-antiplasmin, streptokinase, bivalirudin, and tissue plasminogen activator (t-PA).

Immunosuppressants include, without limitation, cyclosporine, rapamycin and tacrolimus (FK-506), sirolumus, everolimus, etoposide, and mitoxantrone.

Antilipid agents include, without limitation, HMG CoA reductase inhibitors, nicotinic acid, probucol, and fibric acid derivatives (e.g., clofibrate, gemfibrozil, gemfibrozil, fenofibrate, ciprofibrate, and bezafibrate).

Anti-inflammatory agents include, without limitation, salicylic acid derivatives (e.g., aspirin, insulin, sodium salicylate, choline magnesium trisalicylate, salsalate, diflunisal, salicylsalicylic acid, sulfasalazine, and olsalazine), para-amino phenol derivatives (e.g., acetaminophen), indole and indene acetic acids (e.g., indomethacin, sulindac, and etodolac), heteroaryl acetic acids (e.g., tolmetin, diclofenac, and ketorolac), arylpropionic acids (e.g., ibuprofen, naproxen, flurbiprofen, ketoprofen, fenoprofen, and oxaprozin), anthranilic acids (e.g., mefenamic acid and meclofenamic acid), enolic acids (e.g., piroxicam, tenoxicam, phenylbutazone and oxyphenthatrazone), alkanones (e.g., nabumetone), glucocorticoids (e.g., dexamethaxone, prednisolone, and triamcinolone), pirfenidone, and tranilast.

Antineoplastics include, without limitation, nitrogen mustards (e.g., mechlorethamine, cyclophosphamide, ifosfamide, melphalan, and chlorambucil), methylnitrosoureas (e.g., streptozocin), 2-chloroethylnitrosoureas (e.g., carmustine, lomustine, semustine, and chlorozotocin), alkanesulfonic acids (e.g., busulfan), ethylenimines and methylmelamines (e.g., triethylenemelamine, thiotepa and altretamine), triazines (e.g., dacarbazine), folic acid analogs (e.g., methotrexate), pyrimidine analogs (5-fluorouracil, 5-fluorodeoxyuridine, 5-fluorodeoxyuridine monophosphate, cytosine arabinoside, 5-azacytidine, and 2',2'-difluorodeoxycytidine), purine analogs (e.g., mercaptfor use with the present disclosure may, for example, take the form of small molecules, peptides, lipoproteins, polypeptides, polynucleotides encoding polypeptides, lipids, protein-drugs, protein conjugate drugs, enzymes, oligonucleotides and their derivatirubicin, idarubicin, epirubicin, mitoxantrone, bleomycins, plicamycin and mitomycin), phenoxodiol, etoposide, and platinum coordination complexes (e.g., cisplatin and carboplatin).

Antiplatelets include, without limitation, insulin, dipyridamole, tirofiban, eptifibatide, abciximab, and ticlopidine Angiogenic agents include, without limitation, phospholipids, ceramides, cerebrosides, neutral lipids, triglycerides, diglycerides, monoglycerides lecithin, sphingosides, angiotensin fragments, nicotine, pyruvate thiolesters, glycerol-pyruvate esters, dihydoxyacetone-pyruvate esters and monobutyrin.

Anti-angiogenic agents include, without limitation, endostatin, angiostatin, fumagillin and ovalicin.

Vitamins include, without limitation, water-soluble vitamins (e.g., thiamin, nicotinic acid, pyridoxine, and ascorbic acid) and fat-soluble vitamins (e.g., retinal, retinoic acid, retinaldehyde, phytonadione, menaqinone, menadione, and alpha tocopherol).

Antimitotics include, without limitation, vinblastine, vincristine, vindesine, vinorelbine, paclitaxel, docetaxel, epipodophyllotoxins, dactinomycin, daunorubicin, doxorubicin, idarubicin, epirubicin, mitoxantrone, bleomycins, plicamycin and mitomycin.

Metalloproteinase inhibitors include, without limitation, TIMP-1, TIMP-2, TIMP-3, and SmaPI.

NO donors include, without limitation, L-arginine, amyl nitrite, glyceryl trinitrate, sodium nitroprusside, molsidomine, diazeniumdiolates, S-nitrosothiols, and mesoionic oxatriazole derivatives NO release stimulators include, without limitation, adenosine.

Anti-sclerosing agents include, without limitation, collagenases, metalloproteinases and collagen synthesis inhibitors including halofuginone.

Vasoactive agents include, without limitation, nitric oxide, adenosine, nitroglycerine, sodium nitroprusside, hydralazine, phentolamine, methoxamine, metaraminol, ephedrine, trapadil, dipyridamole, vasoactive intestinal polypeptides (VIP), arginine, and vasopressin.

Endothelial growth factors include, without limitation, VEGF (Vascular Endothelial Growth Factor) including VEGF-121 and VEG-165, FGF (Fibroblast Growth Factor) including FGF-1 and FGF-2, HGF (Hepatocyte Growth Factor), and Ang1 (Angiopoietin 1).

Beta blockers include, without limitation, propranolol, nadolol, timolol, pindolol, labetalol, metoprolol, atenolol, esmolol, and acebutolol.

Hormones include, without limitation, progestin, insulin, the estrogens and estradiols (e.g., estradiol, estradiol valerate, estradiol cypionate, ethinyl estradiol, mestranol, quinestrol, estrond, estrone sulfate, and equilin).

Statins include, without limitation, mevastatin, lovastatin, simvastatin, pravastatin, atorvastatin, and fluvastatin.

Insulin growth factors include, without limitation, IGF-1 and IGF-2.

Antioxidants include, without limitation, vitamin A, carotenoids and vitamin E.

Membrane stabilizing agents include, without limitation, certain beta blockers such as propranolol, acebutolol, labetalol, oxprenolol, pindolol and alprenololi.

Calcium antagonists include, without limitation, amlodipine, bepridil, diltiazem, felodipine, isradipine, nicardipine, nifedipine, nimodipine and verapamil.

Retinoids include, without limitation, all-trans-retinol, all-trans-14-hydroxyretroretinol, all-trans-retinaldehyde, all-trans-retinoic acid, all-trans-3,4-didehydroretinoic acid, 9-cis-retinoic acid, 11-cis-retinal, 13-cis-retinal, and 13-cis-retinoic acid.

Anti-macrophage substances include, without limitation, NO donors.

Anti-leukocytes include, without limitation, 2-CdA, IL-1 inhibitors, anti-CD 116/CD 18 monoclonal antibodies, monoclonal antibodies to VCAM, monoclonal antibodies to ICAM, and zinc protoporphyrin.

Cyclooxygenase inhibitors include, without limitation, Cox-1 inhibitors and Cox-2 inhibitors (e.g., CELEBREX® and VIOXX®).

immunomodulatory agents include, without limitation, immunosuppressants (see above) and immunostimulants (e.g., levamisole, isoprinosine, Interferon alpha, and Interleukin-2).

ACE inhibitors include, without limitation, benazepril, captopril, enalapril, fosinopril sodium, lisinopril, quinapril, ramipril, and spirapril.

Cell sensitizers to insulin include, without limitation, glitazones, P par agonists and metformin.

Antisense oligonucleotides include, without limitation, resten-NG.

Cardio protectants include, without limitation, VIP, pituitary adenylate cyclase-activating peptide (PACAP), apoA-I milano, amlodipine, nicorandil, cilostaxone, and thienopyridine.

Petidose inhibitors include, without limitation, omnipatrilat.

Anti-restenotics include, without limitation, include vincristine, vinblastine, actinomycin, epothilone, paclitaxel, and paclitaxel derivatives (e.g., docetaxel). Miscellaneous compounds include, without limitation, Adiponectin.

Although various exemplary embodiments of the present invention have been disclosed, it will be apparent to those skilled in the art that various changes and modifications can be made which will achieve some of the advantages of the invention without departing from the spirit and scope of the invention. It will be apparent to those reasonably skilled in the art that other components performing the same functions may be suitably substituted. Accordingly, it is intended to embrace all such alternatives, modifications and variations that fall within the spirit and scope of the appended claims.

What is claimed is:

1. A stent comprising:
an abluminal surface; and
a plurality of discrete islands of first material deposited on the abluminal surface,
wherein each of the islands of first material has an outer surface and each of the islands comprises:
an inner section of first material having an inner height $L_1$ extending outwardly from the abluminal surface; and
an outer section of first material disposed about the inner section and having an outer height $L_2$ extending outwardly from the abluminal surface,
wherein the outer surface of each island is defined at least by the inner height of the inner section and the outer height of the outer section,
wherein the first material comprises a first polymer and a first drug,
wherein the outer height $L_2$ is greater than the inner height $L_1$, and
wherein the first drug is released from the outer section of first material at a first rate of release, and the first drug is released from the inner section of first material at a second rate of release, wherein the second rate is greater than the first rate.

2. The stent of claim 1, wherein the outer section of first material comprises:
an upper portion;
an intermediate portion; and
a lower portion,
wherein the upper portion is furthest away from the abluminal surface, the lower portion is closest to the abluminal surface, and intermediate portion is between the upper portion portion and the lower portion, and
wherein the first drug is released at a faster rate from the upper portion than the first drug is released from the intermediate portion, and the first drug is released from the intermediate portion at a faster rate than the first drug is released from the lower portion.

3. The stent of claim 1, wherein the plurality of discrete islands comprises an index island relative to which each of the other islands of the plurality of islands is positioned.

4. The stent of claim 1, wherein adjacent islands are separated from one another by a portion of the abluminal surface that is substantially free of deposited first material.

5. The stent of claim 1, further comprising:
a plurality of discrete islands of second material deposited on the abluminal surface,
wherein the second material comprises a second polymer and a second drug,
wherein the second material is different than the first material, and
wherein each of the islands of second material comprises:
an inner section of second material having an inner height $IL_1$ extending outwardly from the abluminal surface; and
an outer section of second material disposed about the inner section and having an outer height $IL_2$ extending outwardly from the abluminal surface, and
wherein the outer height $IL_2$ is greater than the inner height $IL_1$.

6. The stent of claim 5, wherein adjacent islands of first and second material are separated from one another by a portion of the abluminal surface that is substantially free of deposited first or second material.

7. The stent of claim 5, wherein, for a first island of first material and an adjacent island of second material:
the first island of first material comprises the first polymer and the first drug at a first ratio, by weight, to one another; and
the second island of second material comprises the second polymer and the second drug at a second ratio, by weight, to one another,
wherein the first drug is not the same as the second drug.

8. The stent of claim 1, wherein:
the inner section comprises a second material.

9. The stent of claim 8, wherein:
the first material comprises the first polymer and the first drug at a first ratio, by weight, to one another; and
the second material comprises a second polymer and a second drug at a second ratio, by weight, to one another, wherein the first drug is different from the second drug.

10. The stent of claim 1, wherein:
at least one island of the plurality of islands of first material is disposed on another island of the plurality of islands.

11. The stent of claim 1, wherein at least a portion of the abluminal surface comprises a therapeutic amount of a first medicinal compound deposited thereon.

12. The stent of claim 1, wherein:
no island of the plurality of islands of first material is disposed on another island of the plurality of islands of first material.

13. The stent of claim 1, wherein a first ratio of first polymer to first drug is in a range of 1:1 to 2:1 by weight.

14. The stent of claim 1, wherein:
the inner section is a first elliptical portion; and
the outer section is a second elliptical portion.

15. The stent of claim 1, wherein:
the inner section is a ring having a first radius $R_1$; and
the outer section is a ring having an inner radius substantially equal to the first radius $R_1$ and an outer radius $R_2$, wherein the second radius $R_2$ is greater than the first radius $R_1$.

16. The stent of claim 1, wherein the first material comprises the first polymer and the first drug at a first ratio, by weight, to one another and wherein the first ratio is constant.

* * * * *